United States Patent

Hoffmockel et al.

[11] Patent Number: 5,872,263
[45] Date of Patent: Feb. 16, 1999

[54] PROCESS FOR SEPARATING FORMALDEHYDE AND TRIOXANE

[75] Inventors: Michael Hoffmockel, Niederhausen; Karl-Friedrich Mück; Günter Sextro, both of Wiesbaden, all of Germany

[73] Assignee: Hoechst Aktiengesellschaft, Germany

[21] Appl. No.: 431,100

[22] Filed: Apr. 28, 1995

[30] Foreign Application Priority Data

May 2, 1994 [DE] Germany .................. 44 15 332.5

[51] Int. Cl.⁶ .................................. C07D 323/06
[52] U.S. Cl. ................. 549/368; 568/463; 568/466
[58] Field of Search .............. 549/368; 568/463, 568/466

[56] References Cited

U.S. PATENT DOCUMENTS 2,304,080  12/1942  Frank ........................... 260/340
3,496,192   2/1970  Ackerman et al. .............. 260/340

FOREIGN PATENT DOCUMENTS 1 236 473  5/1988  Canada .
1 012 372  12/1965  United Kingdom .
1 118 013   6/1968  United Kingdom .

OTHER PUBLICATIONS

JP-A 59 25387, English Abstract, 1982.

Primary Examiner—Ba K. Trinh
Attorney, Agent, or Firm—Connolly & Hutz

[57] ABSTRACT

A process for separating a gaseous reaction mixture in the preparation of trioxane is described, in which a) the gaseous mixture leaving the reactor is scrubbed in countercurrent with an organic solvent whose boiling point is above 135° C. in which the trioxane predominantly dissolves and which leaves the formaldehyde predominantly in the gas phase which is returned to the reactor, b) the trioxane together with residual formaldehyde is stripped from the solvent by distillation via a column, the overhead product being partially condensed in the temperature range from 62° to 100° C. c) some of the resulting condensate is applied to the column as reflux and some is taken off as product and d) the non-condensed portion is returned to the scrubbing step a).

4 Claims, 3 Drawing Sheets

Fig. 3
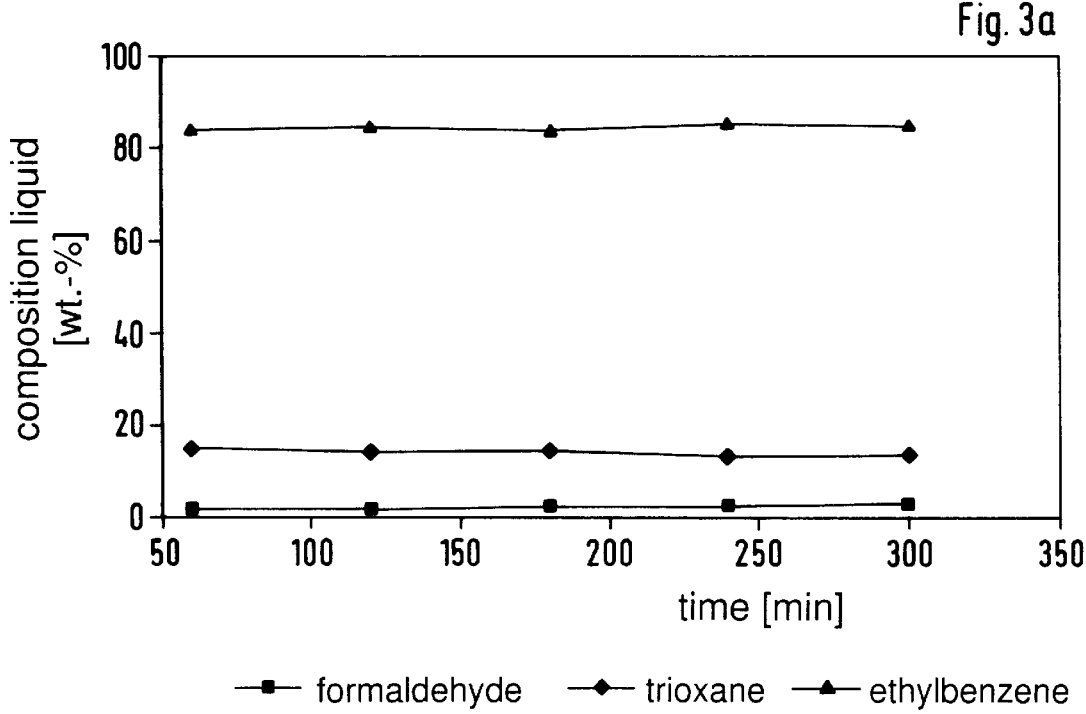
Fig. 3a
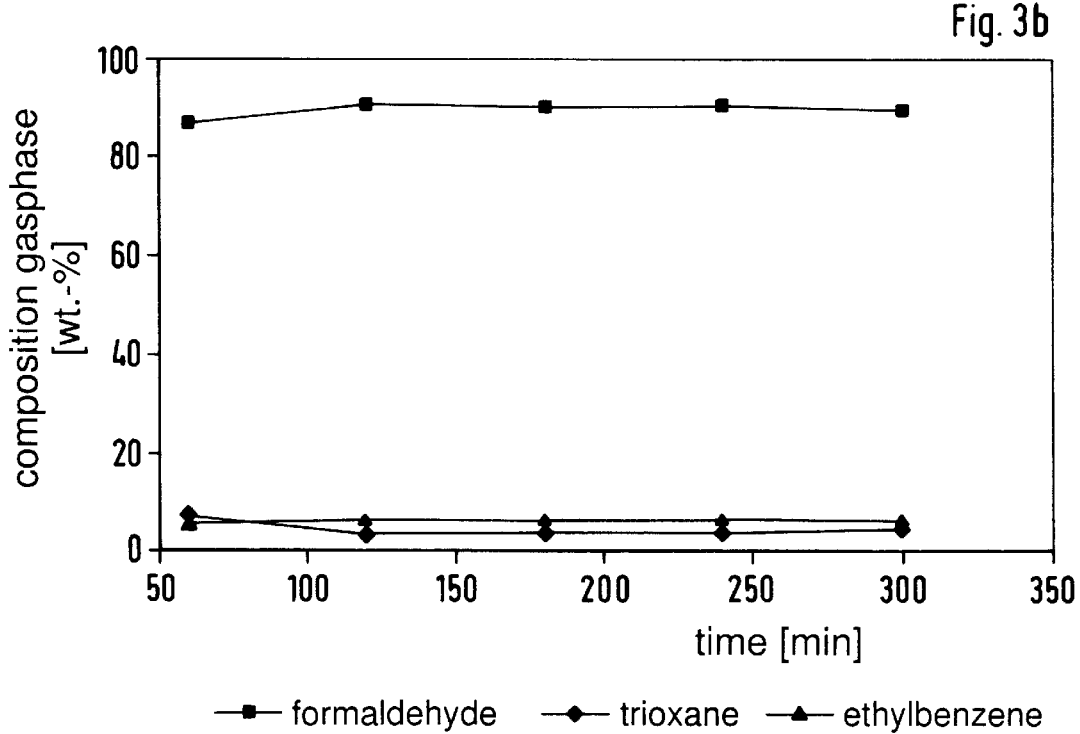
Fig. 3b

PROCESS FOR SEPARATING FORMALDEHYDE AND TRIOXANE

The invention relates to a process for separating mixtures of formaldehyde and trioxane, as result for example in the trimerization of anhydrous formaldehyde in the gas phase.

Trioxane can be prepared from aqueous formaldehyde solutions using acid catalysts. The trioxane is separated off from the reaction mixture by extraction and distillation process steps (U.S. Pat. No. 2, 304, 080, GB-B 1 012 372, DE-A 1 668 867, DE-A 1 543 815). The extraction may be replaced by a crystallization step (DE-A 3 508 668). In these processes for separating formaldehyde and trioxane, water is always present.

In addition, processes are known which make possible the preparation of trioxane from formaldehyde in the gas phase (German Patent Application P 42 44 582.5 of 31.12.92, German Patent Application P 43 00 138.6 of 06.01.93 (each entitled "Process for the preparation of trioxane"), DE-C 1 593 990, JP-A 59/25387). Trimerization in the gas phase, in addition to the higher conversion rates, has the advantage that the energy-consuming removal of water from the reaction mixture is dispensed with. In contrast to the separation of aqueous mixtures, a separation of non-aqueous mixtures has not yet been described.

The object was therefore to find a process by which the reaction mixture of formaldehyde and trioxane can be separated in the absence of water.

The object was achieved by the invention. It describes a process for separating a gaseous reaction mixture in the preparation of trioxane, which mixture contains as main product formaldehyde and trioxane, in which process a) the gaseous mixture leaving the reactor is scrubbed in countercurrent with an organic solvent whose boiling point is above 135° C. in which the trioxane predominantly dissolves and which leaves the formaldehyde predominantly in the gas phase which is returned to the reactor, b) the trioxane together with residual formaldehyde is stripped from the solvent by distillation via a column, the overhead product being partially condensed in the temperature range from 62° to 100° C., preferably 65° to 80° C., c) some of the resulting condensate is applied to the column as reflux and some is taken off as product and d) the non-condensed portion is returned to the scrubbing step a).

The term "predominantly" indicates that under the conditions used in practice complete absorption obviously does not take place or that a small proportion of formaldehyde is always bound in the scrubbing solvent. However, the optimal conditions can only be derived from practice.

Solvents which are suitable are those which have a boiling point ≧135° C. and which are inert towards formaldehyde and trioxane, e.g. saturated aliphatic and aromatic hydrocarbons and saturated aliphatic and aromatic ethers and polyethers. Alkylated aromatics have proved to be advantageous. Particularly good results have been obtained with ethylbenzene, the various xylenes and diethylbenzenes.

BRIEF DESCRIPTION OF THE DRAWINGS

FIGS. 3a and b are plots illustrating that the compositions of the liquid and gas phase change only insignificantly with time.

Figure 1:
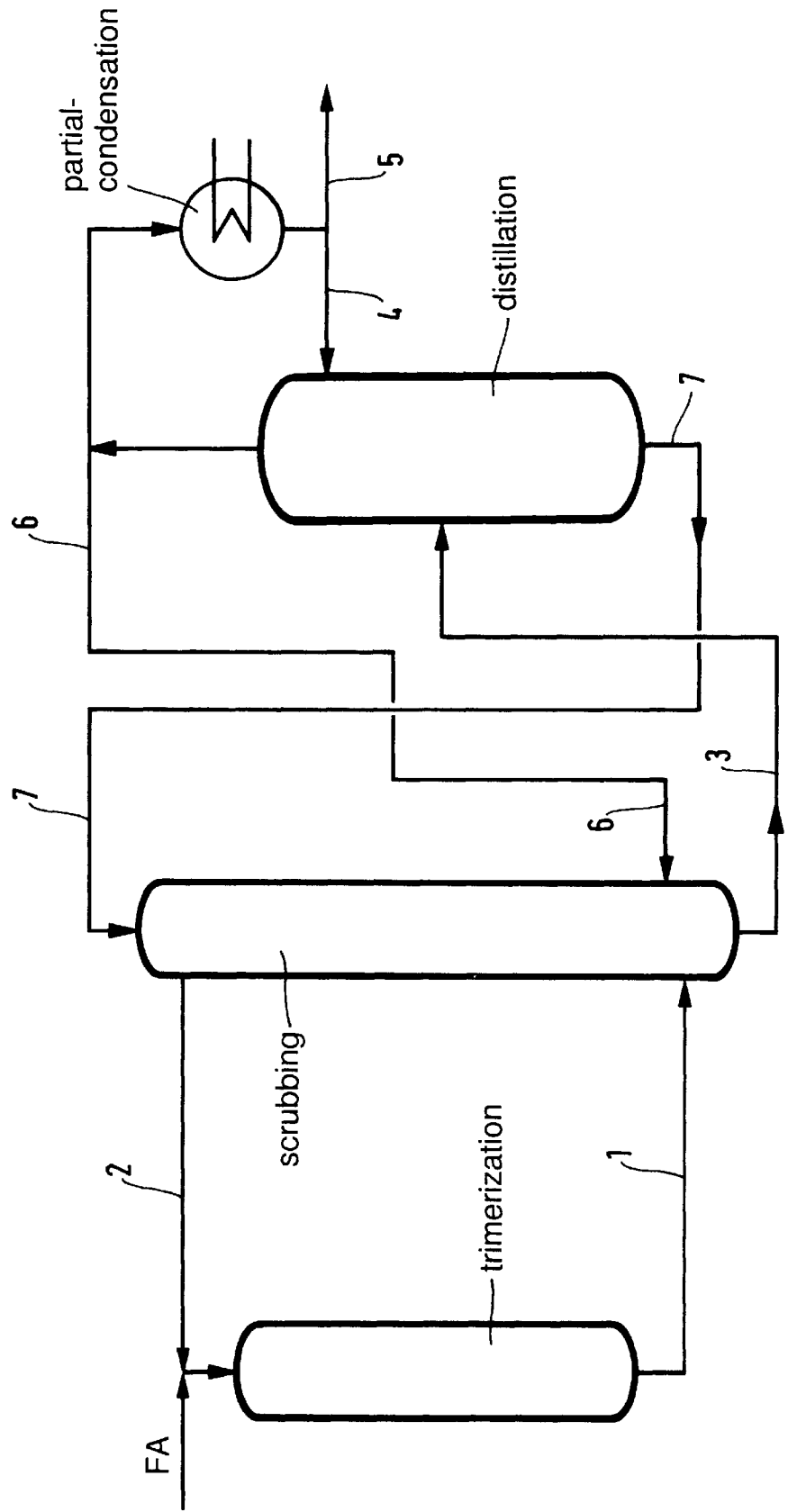
FIG. 1 is a schematic view of a process for separating mixtures of formaldehyde and trioxane, according to the present invention.

One embodiment of the process (including the trimerization step) is outlined in FIG. 1. The anhydrous formaldehyde (FA) is trimerized in the gas phase. The product stream (1) is scrubbed in countercurrent in the scrubber by the solvent. The trioxane substantially dissolves during this; the formaldehyde containing minor amounts of trioxane and solvent is returned (2) to the trimerization reactor. After leaving the scrubber the solvent containing the dissolved trioxane (3) is separated in a distillation column. The bottom stream (7) is freed of trioxane and is reused for the scrubber. The overhead product is partially condensed (temperature range 62° to 100° C., preferably 65° to 80° C.). The non-condensed portions are returned (6) to the scrubber; of the condensed portions, a part-stream is applied (4) as reflux to the distillation column and the other part-stream is taken off as product stream (5). If necessary, this stream (5) can be finely purified by further distillation steps, for example to separate off the residual dissolved formaldehyde.

Experimental description

Two series of experiments were carried out.

EXAMPLE 1

Figure 2:
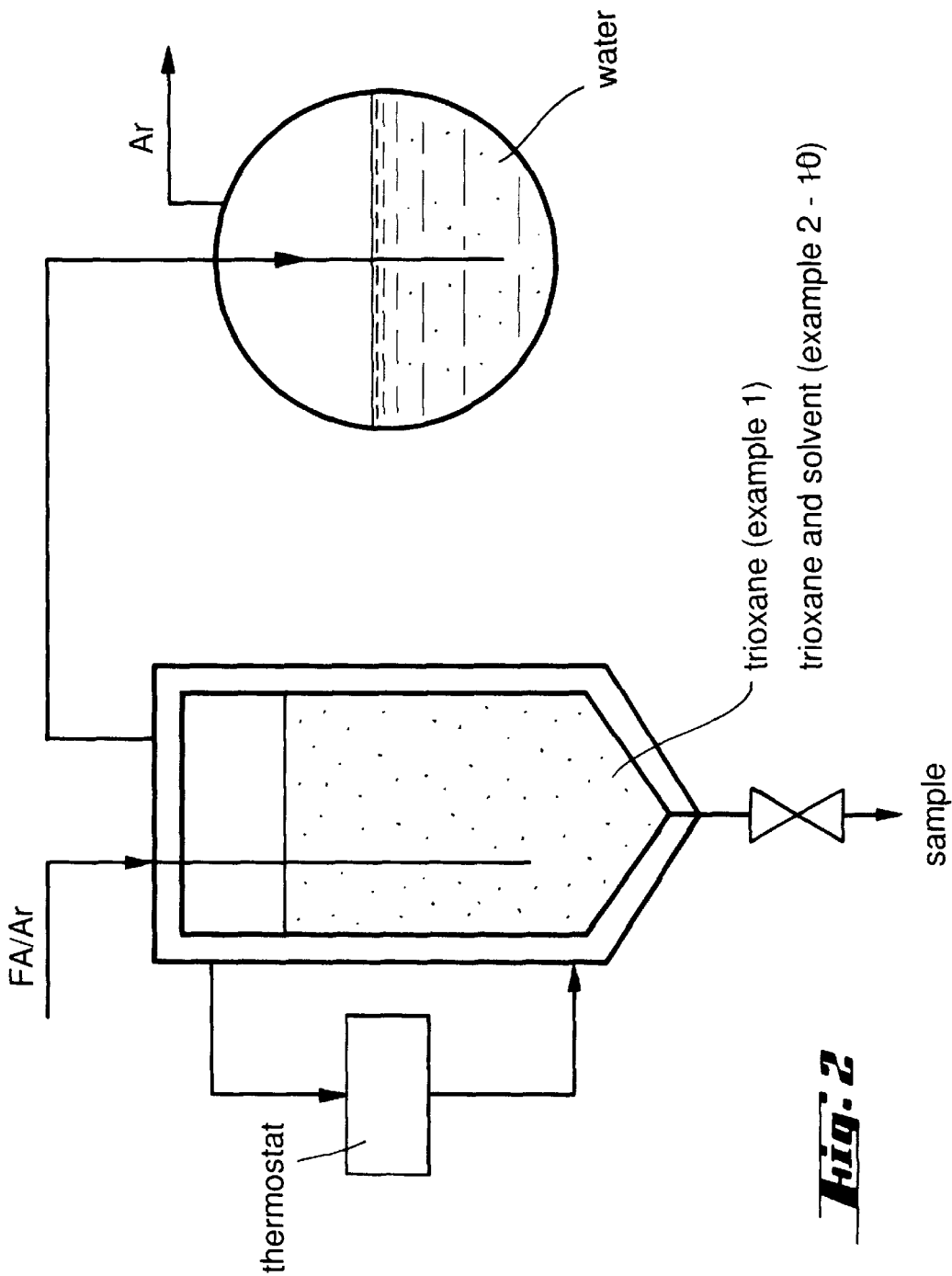
FIG. 2 is a schematic view illustrating the manner of determining the solubility of formaldehyde in trioxane and the composition of the associated gas phase.

The solubility of formaldehyde in trioxane and the composition of the associated gas phase were determined in equipment as in FIG. 2. Trioxane was introduced into a thermostated double-walled vessel having a bottom discharge. Formaldehyde, prepared by decomposition of cyclohexylhemiformal, was passed through molten trioxane at 70° C. During the experimental period of 140 minutes, samples of trioxane were taken via the bottom discharge 4 and collected in ten times the volume of water. The samples were analyzed by gas chromatography; 1.3 to 1.7 per cent by mass formaldehyde were found in the trioxane. The gas stream was collected in water. In the water at the end of the experiment formaldehyde and trioxane were found in a ratio of 1:1. This experimental arrangement can serve as a model for the partial condensation of the overhead stream of the distillation column (compositions of the streams (4) and (6)).

EXAMPLES 2 to 12

In these experiments the equilibrium compositions which are established during scrubbing with the solvent were determined. The arrangement corresponds to that of Example 1 (FIG. 2). In these experiments, the solvent was introduced in a mixture with trioxane into the thermostated vessel. Formaldehyde was introduced over an experimental period of 5 hours. Samples of the liquid were taken and the water which serves as absorption medium was changed in an hourly cycle. Both the water and the samples of the organic solvent were analyzed by gas chromatography. As is shown in FIGS. 3a and b, the compositions of the gas phase and of the liquid change only insignificantly with time. The compositions averaged over time which were established in Examples 2 to 12 are summarized in Table 1. The solvent, the solvent temperature and the solvent loading with trioxane were changed. This experimental arrangement can serve as a model for scrubbing with the solvent (compositions of the streams (2) and (3)).

TABLE 1

| Example number | Solvent | Temperature [°C.] | Liquid [percent by mass] | | | Gas phase [percent by mass] | | | Separation factor[1] |
|---|---|---|---|---|---|---|---|---|---|
| | | | Formaldehyde | Trioxane | Solvent | Formaldehyde | Trioxane | Solvent | |
| 2 | Ethylbenzene | 32 | 1.8 | 13.9 | 84.3 | 90.9 | 3.0 | 6.1 | 234 |
| 3 | Ethylbenzene | 40 | 1.5 | 14.0 | 84.5 | 84.4 | 5.3 | 10.3 | 148 |
| 4 | Ethylbenzene | 50 | 1.4 | 12.5 | 86.1 | 80.9 | 7.0 | 12.1 | 103 |
| 5 | Xylene[2] | 25 | 1.9 | 13.5 | 84.6 | 91.6 | 3.0 | 5.4 | 217 |
| 6 | Xylene | 32 | 1.3 | 15.0 | 83.7 | 80.3 | 3.9 | 15.8 | 237 |
| 7 | Xylene | 40 | 1.5 | 12.3 | 86.2 | 85.3 | 6.5 | 8.2 | 108 |
| 8 | Xylene | 50 | 0.9 | 12.0 | 87.1 | 77.6 | 8.9 | 8.9 | 117 |
| 9 | Xylene | 50 | 1.1 | 22.2 | 76.3 | 71.8 | 14.7 | 12.5 | 99 |
| 10 | Xylene | 50 | 1.7 | 28.7 | 69.6 | 75.8 | 15.2 | 9.0 | 84 |
| 11 | Diethyl-benzene[3] | 32 | 1.5 | 14.5 | 84.0 | 92.6 | 3.2 | 4.2 | 280 |
| 12 | Diethyl-benzene | 50 | 1.2 | 23.4 | 75.4 | 77.3 | 12.9 | 9.8 | 116 |

[1] Separation factor = $(TOX_l * FA_g)/(TOX_g * FA_l)$
[2] Mixture of isomers of o,p-xylene
[3] Mixture of isomers of o,p-diethylbenzene

We claim:

1. A process for separating a gaseous reaction mixture in the preparation of trioxane, which mixture contains as main product formaldehyde and trioxane, In which process a) the gaseous mixture leaving the reactor is scrubbed in counter-current with an organic solvent whose boiling point is above 135° C. in which the trioxane predominantly dissolves and which leaves the formaldehyde predominantly in the gas phase which is returned to the reactor, b) the trioxane together with residual formaldehyde is stripped from the solvent by distillation via a column, the overhead product being partially condensed in the temperature range from 62° to 100° C. c) some of the resulting condensate is applied to the column as reflux and some is taken off as product and d) the non-condensed portion is returned to the scrubbing step a).

2. The process as claimed in claim 1, wherein the temperature range is 65° to 80° C.

3. The process as claimed in claim 1, wherein the solvent used is saturated aliphatic and aromatic hydrocarbons or aliphatic and aromatic ethers and polyethers.

4. The process as claimed in claim 1, wherein the solvent used is ethylbenzene, the various xylenes or diethylbenzenes are used.

* * * * *